United States Patent [19]

Oh-Kita et al.

[11] Patent Number: 5,166,119
[45] Date of Patent: Nov. 24, 1992

[54] PREPARATION OF CATALYSTS FOR PRODUCING METHACROLEIN AND METHACRYLIC ACID

[75] Inventors: Motomu Oh-Kita; Yoshiyuki Taniguchi, both of Otake, Japan

[73] Assignee: Mitsubishi Rayon Co., Ltd., Tokyo, Japan

[21] Appl. No.: 584,217

[22] Filed: Sep. 18, 1990

[30] Foreign Application Priority Data

Sep. 25, 1989 [JP] Japan .................................. 1-248308

[51] Int. Cl.$^5$ .................... B01J 23/78; B01J 23/82; B01J 23/84; B01J 23/88
[52] U.S. Cl. .................................. 502/205; 502/212; 502/226; 502/243; 502/304; 502/306; 502/307; 502/311
[58] Field of Search ............... 502/205, 212, 243, 306, 502/307, 311, 304, 220

[56] References Cited

U.S. PATENT DOCUMENTS

| | | | |
|---|---|---|---|
| 4,035,418 | 7/1977 | Okada et al. | 502/306 X |
| 4,224,193 | 9/1980 | Vanderspurt | 568/477 |
| 4,248,803 | 2/1981 | Vanderspurt | 568/477 |
| 4,707,460 | 11/1987 | Ishii et al. | 502/26 |
| 4,816,603 | 3/1989 | Oh-Kita et al. | 502/205 X |

FOREIGN PATENT DOCUMENTS

| | | |
|---|---|---|
| 0194516 | 9/1986 | European Pat. Off. . |
| 0267556 | 5/1988 | European Pat. Off. . |
| 0279374 | 8/1988 | European Pat. Off. . |
| 0304867 | 3/1989 | European Pat. Off. . |
| 57-12827 | 1/1982 | Japan . |

Primary Examiner—W. J. Shine
Attorney, Agent, or Firm—Armstrong & Kubovcik

[57] ABSTRACT

A method for preparing a multicomponent catalyst including molybdenum, bismuth, iron and cesium or thallium for producing methacrolein and methacrylic acid by the gas-phase catalytic oxidation of isobutylene or tert-butanol with molecular oxygen, wherein an aqueous nitric acid solution containing 0.01 to 0.36 mole of nitric acid per mole of ammonium molybdate, which is a material for the molybdenum component of the catalyst, and at least one material for the bismuth, iron, cesium and thallium components of the catalyst is added to an aqueous solution containing ammonium molybdate and materials for the remaining catalyst components, if any, to obtain a slurry which is then dried and calcined, provided that the nitric acid excludes nitric acid radicals contained in the materials containing the catalyst components. The amount of nitric acid used is controlled in a particular range, so that a highly active catalyst for gas-phase catalytic oxidation is obtained.

4 Claims, No Drawings

PREPARATION OF CATALYSTS FOR PRODUCING METHACROLEIN AND METHACRYLIC ACID

BACKGROUND OF THE INVENTION

1. Field of the Invention

The present invention relates to a method for preparing a catalyst used in producing methacrolein and methacrylic acid by the gas-phase catalytic oxidation of isobutylene or tert-butanol.

2. Description of the Prior Art

A large number of catalysts are known in regard to the production of methacrolein and methacrylic acid by the gas-phase catalytic oxidation of isobutylene or tert-butanol. Also, a large number of methods for producing the catalysts have been proposed. For example, Japanese Patent Application Kokai No. 57 12827 discloses that, in producing a multicomponent catalyst comprising molybdenum, bismuth, lead and antimony used in the ammoxidation of propylene, an aqueous slurry is adjusted to a pH of 7 or less. Further, U.S. Pat. No. 4,224,193 discloses that, in producing a multicomponent catalyst comprising molybdenum, bismuth, iron and an alkali metal (e.g. potassium, rubidium) used in the oxidation of propylene or isobutylene, it is preferred to finally adjust the pH of an aqueous slurry to 1 to 5. However, the above methods are complicated and expensive in producing a catalyst industrially. Further, since these methods require nitric acid or ammonia as a pH controlling agent, they have a problem that a large amount of NOx is generated when drying and baking the catalyst.

SUMMARY OF THE INVENTION

The present inventors have investigated to obtain a highly active catalyst under conditions for producing it industrially and, as a result, found a method for preparing the highly active catalyst using quite a small amount of nitric acid. Thus, the present invention has been completed.

An object of the present invention is to provide a novel method for preparing a catalyst for advantageously producing methacrolein and methacrylic acid from isobutylene or tert-butanol.

According to the present invention, there is provided a method for preparing a multicomponent catalyst comprising molybdenum, bismuth, iron and cesium or thallium for producing methacrolein and methacrylic acid by the gas-phase catalytic oxidation of isobutylene or tert-butanol with molecular oxygen, wherein an aqueous nitric acid solution containing 0.01-0.36 mole of nitric acid, per mole of ammonium molybdate, and at least one material containing a catalyst component other than molybdenum is added to an aqueous solution comprising ammonium molybdate to obtain a slurry which is dried and calcined, provided that nitric acid radicals contained in materials which contain a catalyst component.

DESCRIPTION OF PREFERRED EMBODIMENTS

A catalyst preferably prepared by the method of the present invention is represented by the formula:

wherein Mo, W, Bi, Fe, Sb and O are molybdenum, tungsten, bismuth, iron, antimony and oxygen, respectively, A is at least one element selected from the group consisting of nickel and cobalt, X is at least one element selected from the group consisting of cesium and thallium, Y is at least one element selected from the group consisting of magnesium, manganese, zinc, barium and chromium, Z is at least one element selected from the group consisting of phosphorus, boron, sulfur, silicon, cerium, potassium and rubidium, a, b, c, d, e, f, g, h, i and j are an atomic ratio of each element, and when a is 12, b is 0 to 2, c is 0.01 to 2, d is 0.5 to 5, e is 0.01 to 3, f is 1 to 12, g is 0.01 to 2, h is 0.01 to 10, i is 0 to 20, and j is the number of oxygen atoms necessary to satisfy the valence of each component.

This catalyst is used for producing methacrolein and methacrylic acid by the gas-phase catalytic oxidation of isobutylene or tert-butanol with molecular oxygen.

As a material for molybdenum, one of the constituents of the catalyst, it is desirable to use ammonium molybdate.

As materials for other constituents, it is desirable to use oxides or those which can be turned into an oxide by strong heating such as chlorides, sulfates, nitrates, ammonium salts, carbonates, hydroxides and mixtures thereof.

The characteristics of the present invention include that ammonium molybdate is used as a material for the molybdenum component, and also that the amount of nitric acid used in the aqueous solution of a certain material is as extremely small as 0.01 to 0.36 mole per 1 mole of ammonium molybdate as compared with usually used amounts of nitric acid.

The amount of nitric acid referred to herein means the amount of nitric acid alone added as a solvent to the aqueous solution of the materials, said nitric acid excluding nitric acid radicals usually contained as an anion in the materials for the catalyst.

In the preparation method of the present invention, nitric acid is used for dissolving at least one of the materials for bismuth, iron and the components A and Y contained in the foregoing formula. Particularly, it is preferred to dissolve all of the materials for bismuth, iron and the components A and Y in the aqueous solution containing nitric acid. The resulting aqueous nitric acid solution is added to the aqueous solution of the material for the molybdenum component and a material for the tungsten component added as need arises, to prepare an aqueous slurry. The remaining materials not dissolved in the aqueous solution containing nitric acid may b added in the form of their aqueous solution or a solid to the aqueous solution of the material for the molybdenum and/or tungsten component.

The amount of nitric acid used here must be in the range of amount according to the present invention, not giving a sufficient catalytic activity whether it is smaller than or larger than said range of amount. Because the conventionally prepared catalysts not having a sufficient activity must be used under high-temperature reaction conditions for the industrial production of methacrolein and methacrylic acid, they have a defect of the catalytic life being short.

A reason why a high catalytic activity is obtained only when the particular amount of nitric acid is used is presumed as follows. The molybdenum or tungsten component forms a poly-nuclear metal complex with bismuth, iron, etc. The component A contained in the foregoing formula is particularly difficult to form a polynuclear metal complex, but becomes easy to form the above complex when the amount of nitric acid is in the range of amount according to the present invention. Formation of such the polynuclear metal complex containing also the component A may be considered to develop a high activity.

In the gas-phase catalytic oxidation of isobutylene or tert-butanol, the acidity and basicity of the catalyst is one of the important factors for developing the selectivity of the products (Fine Chemical, Vol. 9, No. 23, pp. 1 to 14, 1980).

In this connection, Japanese Patent Application Kokai No. 61-22040 and No. 63-122642 disclose that an element such as potassium, rubidium, cesium or thallium is added as a component for controlling the acidity and basicity of the catalyst.

However, when the amount of nitric acid is extremely small as in the present invention, cesium and thallium among the foregoing elements are important, it being difficult to obtain a sufficient selectivity when potassium or rubidium is used alone.

The catalyst obtained by the method of the present invention works effectively without a carrier, but can be also used supported on or diluted with an inert carrier such as silica, alumina, silica-alumina, silicon carbide, etc.

In producing methacrolein or methacrylic acid with the catalyst prepared by the method of the present invention, molecular oxygen is added to isobutylene or tert-butanol which is a material, and the gas-phase catalytic oxidation is carried out in the presence of the foregoing catalyst.

The molar ratio of isobutylene or tert-butanol to oxygen is preferably 1:0.5 to 1:3. It is preferred for the gas, a material, to be used diluted with an inert gas.

The molecular oxygen used in the oxidation may be any of pure oxygen gas and air, but air is advantageous industrially.

The reaction pressure is preferably normal pressure to several atmospheres.

The reaction temperature is preferably in a range of 250° to 450° C.

This reaction can be carried out by either a fluidized-bed method or fixed-bed method.

The catalyst obtained by the present invention has advantages that the catalytic activity is extremely high and besides the catalytic life is long.

The present invention will be illustrated in more detail with reference to the following examples, which are however not to be construed to limit the scope of the present invention.

Parts in the following examples and comparative examples are by weight. Analyses were carried out by gas chromatography. The conversion of isobutylene or tert-butanol and the selectivity for the produced methacrolein and methacrylic acid are defined as follows:

$$\text{Conversion of isobutylene or tert-butanol (\%)} = \frac{\text{Number of moles of reacted isobutylene or tert-butanol}}{\text{Number of moles of supplied isobutylene or tert-butanol}} \times 100$$

$$\text{Selectivity for methacrolein or methacrylic acid (\%)} = \frac{\text{Number of moles of produced methacrolein or methacrylic acid}}{\text{Number of moles of reacted isobutylene or tert-butanol}} \times 100$$

EXAMPLE 1

To 1000 parts of pure water were added 500 parts of ammonium molybdate and 27.6 parts of cesium nitrate, and the resulting mixture was heated with stirring (solution A).

Separately, 10 parts of 60% nitric acid was added to 80 parts of pure water, and after the resulting solution was made homogeneous, 68.7 parts of bismuth nitrate was added to and dissolved in the solution. To the solution were successively added 190.7 parts of ferric nitrate, 274.5 parts of nickel nitrate, 137.3 parts of cobalt nitrate, 121.0 parts of magnesium nitrate and then 720 parts of pure water, and these salts were dissolved to make a solution (solution B).

The solution B was added to the solution A to make a slurry, and 24.1 parts of antimony trioxide was added thereto. The mixture was heated with stirring to vaporize the greater part of water. The molar ratio of nitric acid to ammonium molybdate at that time was 0.24.

The resulting caky substance was dried at 140° C., baked at 500° C. for 6 hours and then formed.

The composition of elements except oxygen of the catalyst thus obtained was $Mo_{12}Bi_{0.6}Fe_2Sb_{0.7}Ni_4Co_2Mg_2Cs_{0.6}$ (catalysts described later also are represented by the composition of elements except oxygen).

This catalyst was charged in a stainless steel tubular reactor, and a mixed gas, a material, consisting of 5 vol.% of isobutylene, 12 vol.% of oxygen, 10 vol.% of steam and 73 vol.% of nitrogen was passed through the catalyst layer for a contact time of 3.6 seconds to react the mixed gas at 360° C.

As a result, the conversion of isobutylene was 94.5%, the selectivity for methacrolein was 85.3% and the selectivity for methacrylic acid was 5.0%.

EXAMPLE 2

To 1000 parts of pure water were added 500 parts of ammonium molybdate and 27.6 parts of cesium nitrate, and the resulting mixture was heated with stirring (solution A).

Separately, 5 parts of 60% nitric acid was added to 50 parts of pure water, and after the resulting solution was made homogeneous, 68.7 parts of bismuth nitrate was added to and dissolved in the solution. To the solution were added 480.7 parts of cobalt nitrate and 200 parts of pure water, and this salt was dissolved in the solution (solution B).

Further separately, 190.7 parts of ferric nitrate and 70.2 parts of zinc nitrate were added to and dissolved in 600 parts of pure water (solution C). The solution B was added to the solution A to make a slurry, and then the solution C was added to the slurry. The molar ratio of nitric acid to ammonium molybdate at that time was 0.12.

Thereafter, 24.1 parts of antimony trioxide was added, and the slurry was heated with stirring and spray-dried.

The dried substance obtained was baked at 500° C. for 6 hours and then formed.

The composition of the catalyst thus obtained was $Mo_{12}Bi_{0.6}Fe_2Sb_{0.7}Co_7Zn_1Cs_{0.6}$.

Using this catalyst, reaction was carried out under the same conditions as in Example 1. As a result, the conversion of isobutylene was 93.2%, the selectivity for methacrolein was 87.3% and the selectivity for methacrylic acid was 4.4%.

EXAMPLES 3 to 8

The catalysts shown in Table 1 were prepared according to Example 1 except that nitric acid was used in amounts shown in Table 1 and that a material for tungsten was ammonium tungstate; those for chromium, thallium, barium, cerium, potassium, rubidium, manganese and zinc were their nitrates, respectively; those for boron, sulfur and phosphorus were boric acid, sulfuric acid and phosphoric acid, respectively; and that for silicon was silica sol.

TABLE 1

| Example | Nitric acid (mole) Ammonium molybdate (mole) | Composition of catalyst |
| --- | --- | --- |
| 3 | 0.30 | $Mo_{12}W_{0.3}Bi_{0.6}Fe_2Sb_{0.7}Ni_4Co_2Mg_{0.5}Zn_{0.5}Cs_{0.6}$ |
| 4 | 0.20 | $Mo_{12}W_{0.3}Bi_{0.5}Fe_2Sb_{1.5}Ni_4Co_2Zn_1Cr_{0.3}B_{0.5}Cs_{0.3}Tl_{0.1}$ |
| 5 | 0.25 | $Mo_{12}W_{0.3}Bi_{0.7}Fe_2Sb_{0.7}Ni_4Co_2Mg_1B_{0.5}S_{0.07}Cs_{0.4}$ |
| 6 | 0.04 | $Mo_{12}W_{0.3}Bi_{0.7}Fe_2Sb_{0.7}Ni_4Co_2Zn_1Ce_{0.5}Si_5Cs_{0.5}K_{0.1}$ |
| 7 | 0.07 | $Mo_{12}W_{0.3}Bi_{0.6}Fe_2Sb_{0.7}Ni_4Co_2Mg_{15}Cs_{0.4}Rb_{0.1}$ |
| 8 | 0.12 | $Mo_{12}W_{0.3}Bi_{0.6}Fe_2Sb_{15}Ni_4Mg_1Mn_{0.5}P_{0.08}Tl_{0.7}$ |

Using these catalysts, reaction was carried out under the same conditions as in Example 1 except that the reaction temperature was changed to 350° C. The results are shown in Table 2.

TABLE 2

| Example | Conversion of isobutylene (%) | Selectivity for methacrolein (%) | Selectivity for methacrylic acid (%) |
| --- | --- | --- | --- |
| 3 | 97.1 | 88.4 | 3.6 |
| 4 | 98.0 | 88.0 | 3.3 |
| 5 | 97.3 | 88.1 | 3.5 |
| 6 | 98.1 | 86.6 | 4.0 |
| 7 | 97.3 | 88.3 | 3.4 |
| 8 | 97.9 | 87.7 | 3.2 |

EXAMPLES 9 AND 10

Using the catalyst of Example 1 in Example 9 and that of Example 3 in Example 10, reaction was carried out under the same conditions as in Example 1 except that the material for the reaction was changed from isobutylene to tert-butanol, and that reaction temperatures shown in Table 3 were used. The results are also shown in Table 3.

TABLE 3

| Example | Reaction temperature (°C.) | Conversion of tert-butanol (%) | Selectivity for methacrolein (%) | Selectivity for methacrylic acid (%) |
| --- | --- | --- | --- | --- |
| 9 | 360 | 100 | 83.3 | 2.5 |
| 10 | 350 | 100 | 87.4 | 2.7 |

COMPARATIVE EXAMPLE 1

In Example 1, a catalyst of the same composition was prepared in the same manner as in Example 1 except that nitric acid was not added. Using this catalyst, reaction was carried out under the same conditions as in Example 1 to find that the conversion of isobutylene was 92.0%, the selectivity for methacrolein was 85.2% and the selectivity for methacrylic acid was 4.5%.

COMPARATIVE EXAMPLE 2

In Example 1, a catalyst of the same composition was prepared in the same manner as in Example 1 except that the amount of nitric acid was 0.5 mole per 1 mole of ammonium molybdate. Using this catalyst, reaction was carried out under the same conditions as in Example 1 to find that the conversion of isobutylene was 92.1%, the selectivity for methacrolein was 85.0% and the selectivity for methacrylic acid was 4.8%.

COMPARATIVE EXAMPLE 3

In Example 1, reaction was carried out under the same conditions as in Example 1 except that the amount of nitric acid was 1.0 mole per 1 mole of ammonium molybdate, and that tert-butanol was used as a material for the reaction. As a result, the conversion of tert-butanol was 100%, the selectivity for methacrolein was 81.0% and the selectivity for methacrylic acid was 2.0%.

COMPARATIVE EXAMPLE 4

In Example 3, reaction was carried out under the same conditions as in Example 1 except that the amount of nitric acid was 0.001 mole per 1 mole of ammonium molybdate, and that the reaction temperature was 350° C. As a result, the conversion of isobutylene was 95.1%, the selectivity for methacrolein was 88.5% and the selectivity for methacrylic acid was 3.2%. When the amount of nitric acid is reduced, the activity of the prepared catalyst lowers, and the conversion of isobutylene shows as large a reduction as about 2% at the same reaction temperature.

COMPARATIVE EXAMPLE 5

In Example 3, reaction was carried out under the same conditions as in Example 1 except that the amount of nitric acid was 2.0 moles per 1 mole of ammonium molybdate, and that the reaction temperature was 350° C. As a result, the conversion of isobutylene was 95.0%, the selectivity for methacrolein was 88.6% and the selectivity for methacrylic acid was 3.3%. When the amount of nitric acid is increased, the catalytic activity similarly lowers.

COMPARATIVE EXAMPLE 6

Using the catalyst used in Comparative Example 5, reaction was carried out under the same conditions as in Comparative Example 5 except that tert-butanol was used as a material for the reaction. As a result, the conversion of tert-butanol was 100%, the selectivity for methacrolein was 85.1% and the selectivity for methacrylic acid was 2.8%. In this case, the conversion of tert-butanol was the same as in Example 10 but the selectivity for methacrolein lowered.

COMPARATIVE EXAMPLE 7

In Example 3, a catalyst of the following composition was prepared in the same manner as in Example 3 except that 14.3 parts of potassium nitrate was used in place of cesium nitrate:

$$Mo_{12}W_{0.3}Bi_{0.6}Fe_2Sb_{0.7}Ni_4Co_2Mg_{0.5}Zn_{0.5}K_{0.6}.$$

Using this catalyst, reaction was carried out under the same conditions as in Example 1 except that the reaction temperature was 350° C. As a result, the conversion of isobutylene was 98.5%, the selectivity for methacrolein was 83.1% and the selectivity for methacrylic acid was 4.5%.

COMPARATIVE EXAMPLE 8

In Example 3, a catalyst of the following composition was prepared in the same manner as in Example 3 except that 20.9 parts of rubidium nitrate was used in place of cesium nitrate:

$$Mo_{12}W_{0.3}Bi_{0.6}Fe_2Sb_{0.7}Ni_4Co_2Mg_{0.5}Zn_{0.5}Rb_{0.6}.$$

Using this catalyst, reaction was carried out under the same conditions as in Example 1 except that reaction temperature was 350° C. As a result, the conversion of isobutylene was 98.0%, the selectivity for methacrolein was 85.3% and the selectivity for methacrylic acid was 4.0%.

What is claimed is:

1. A method for preparing a multicomponent catalyst comprising molybdenum, bismuth, iron and cesium or thallium for producing methacrolein and methacrylic acid by the gas-phase catalytic oxidation of isobutylene or tert-butanol with molecular oxygen, wherein an aqueous nitric acid solution containing 0.01 to 0.36 mole of nitric acid, per mole of ammonium molybdate which is a material for a molybdenum component of the catalyst, and at least one material for the bismuth, iron and cesium or thallium components is added to an aqueous solution containing ammonium molybdate and materials for the remaining catalyst components, if any, to obtain a slurry which is then dried and calcined, provided that said nitric acid excludes nitric acid radicals contained in the materials containing the catalyst components.

2. A method according to claim 1, wherein said multicomponent catalyst comprises molybdenum, bismuth, iron, antimony and cesium or thallium, and said slurry contains also a material for the antimony component.

3. A method according to claim 1, wherein said multicomponent catalyst is represented by the formula:

$$Mo_aW_bBi_cFe_dSb_eA_fX_gY_hZ_iO_j$$

wherein Mo, W, Bi, Fe, Sb and O are molybdenum, tungsten, bismuth, iron, antimony and oxygen, respectively, A is at least one element selected from the group consisting of nickel and cobalt, X is at least one element selected from the group consisting of cesium and thallium, Y is at least one element selected from the group consisting of magnesium, manganese, zinc, barium and chromium, Z is at least one element selected from the group consisting of phosphorus, boron, sulfur, silicon, cerium, potassium and rubidium, a, b, c, d, e, f, g, h, i and j are an atomic ratio of each element, and when a is 12, b is 0 to 2, c is 0.01 to 2, d is 0.5 to 5, e is 0.01 to 3, f is 1 to 12, g is 0.01 to 2, h is 0.01 to 10, i is 0 to 20, and j is the number of oxygen atoms necessary to satisfy the valence of each component, and said slurry comprises materials for the components of the catalyst.

4. A method according to claim 3, wherein at least one of the materials for bismuth, iron and the components A and Y is dissolved in an aqueous solution containing 0.01 to 0.36 mole of nitric acid per 1 mole of ammonium molybdate and said nitric acid excludes nitric acid radicals contained in the materials for the catalyst.

* * * * *